US009855747B2

(12) United States Patent
Yoshida et al.

(10) Patent No.: US 9,855,747 B2
(45) Date of Patent: Jan. 2, 2018

(54) INKJET HEAD AND INKJET DEVICE

(71) Applicant: Panasonic Intellectual Property Management Co., Ltd., Osaka (JP)

(72) Inventors: Hidehiro Yoshida, Hyogo (JP); Kazuki Fukada, Osaka (JP); Kenichi Yamamoto, Osaka (JP); Takeshi Kita, Hyogo (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 15/324,084

(22) PCT Filed: Sep. 4, 2015

(86) PCT No.: PCT/JP2015/004485
§ 371 (c)(1),
(2) Date: Jan. 5, 2017

(87) PCT Pub. No.: WO2016/042722
PCT Pub. Date: Mar. 24, 2016

(65) Prior Publication Data
US 2017/0203567 A1 Jul. 20, 2017

(30) Foreign Application Priority Data
Sep. 17, 2014 (JP) .................. 2014-188966

(51) Int. Cl.
*B41J 2/14* (2006.01)
*B41J 2/18* (2006.01)
(Continued)

(52) U.S. Cl.
CPC ....... *B41J 2/14233* (2013.01); *B41J 2/14201* (2013.01); *B41J 2/17566* (2013.01);
(Continued)

(58) Field of Classification Search
CPC ...... B41J 2/14233; B41J 2/18; B41J 2/14201; B41J 2/17566; B41J 25/001; B41J 2002/14306
See application file for complete search history.

(56) References Cited

U.S. PATENT DOCUMENTS 6,254,222 B1 7/2001 Murata et al.
9,205,665 B2 * 12/2015 Kaneko ............... B41J 2/17596
(Continued)

FOREIGN PATENT DOCUMENTS

JP 9-277531 10/1997
JP 11-227208 8/1999
(Continued)

OTHER PUBLICATIONS

International Search Report of PCT application No. PCT/JP2015/004485 dated Dec. 1, 2015.
(Continued)

*Primary Examiner* — Geoffrey Mruk
(74) *Attorney, Agent, or Firm* — Panasonic IP Management; Kerry S. Culpepper

(57) ABSTRACT

An inkjet head, includes: a pressure chamber communicating with an ink flow channel; a diaphragm linked to the pressure chamber; a piezoelectric element linked to the diaphragm; a nozzle communicating with the pressure chamber; and a vibrating mechanism placed in the ink flow channel and vibrates a supplied ink. Further provided is an inkjet device, including: the above inkjet head; a holding unit that holds a coating object; a moving mechanism that causes relative movement between the inkjet head and the holding unit; and a control unit that controls the inkjet head, the holding unit, and the moving mechanism.

13 Claims, 6 Drawing Sheets

(51) Int. Cl.
  *B41J 25/00* (2006.01)
  *B41J 2/175* (2006.01)
(52) U.S. Cl.
  CPC ............... *B41J 2/18* (2013.01); *B41J 25/001* (2013.01); *B41J 2002/14306* (2013.01)

(56) References Cited

U.S. PATENT DOCUMENTS

| | | |
|---|---|---|
| 2003/0020788 A1 | 1/2003 | Asano |
| 2011/0109702 A1 | 5/2011 | Kim et al. |
| 2011/0129892 A1 | 6/2011 | Umezu et al. |
| 2011/0280098 A1 | 11/2011 | Shiono |
| 2012/0200649 A1 | 8/2012 | Igawa et al. |
| 2013/0302872 A1 | 11/2013 | Umezu et al. |

FOREIGN PATENT DOCUMENTS

| | | |
|---|---|---|
| JP | 2003-072104 | 3/2003 |
| JP | 2012-035589 A | 2/2012 |
| JP | 5371678 B | 12/2013 |
| JP | 5540304 B | 7/2014 |

OTHER PUBLICATIONS

The Extended European Search Report dated Aug. 22, 2017 for the related European Patent Application No. 15842010.9.

\* cited by examiner

INKJET HEAD AND INKJET DEVICE

TECHNICAL FIELD

The technical field relates to an inkjet head and an inkjet device particularly in the fields of medicine, drug discovery, and biotechnology.

BACKGROUND

In recent years, an inkjet method that makes it possible to discharge a liquid at high speed has been utilized in order to supply a drug solution or a reagent, or in order to carry out three-dimensional-shape patterning using cells, in the fields of medicine, drug discovery, and biotechnology.

In the publication of Japanese Patent No. 5,540,304, one single nozzle is used to discharge a solution including cells. However, patterning based on one single nozzle has a problem of poor productivity. In recent years, it has been desired to discharge solutions by use of multiple nozzles, in order to improve productivity.

Furthermore, a solution including particles such as cells easily causes sedimentation of the particles. If sedimentation of particles occurs, and the particles remain at the same location for a long time, the particles adhere to one another, thus forming into large grains, or the solution including particles becomes inhomogeneous.

Therefore, the publication of Japanese Patent No. 5,371,678 has proposed a circulation method in which a solution including particles is circulated to suppress sedimentation of the particles.

In particular, in cases where a solution including particles such as cells is discharged by using an inkjet head, it is required that a solution that comes into a state in which the cells are homogenously dispersed is prepared while sedimentation of particles is suppressed, and that the solution is discharged to homogenize the density of the solution. Furthermore, in case where a solution including cells is discharged from multiple nozzles, it is also required that cell densities are evened among multiple nozzles.

SUMMARY

The disclosure provides an inkjet head that has multiple nozzles and that evenly supplies cells to the nozzles while suppressing sedimentation of the cells.

The inkjet head according to the disclosure includes: a pressure chamber that is communicated with an ink flow channel; a diaphragm that is linked to the pressure chamber; a piezoelectric element that is linked to the diaphragm; and a nozzle that is communicated with the pressure chamber. Furthermore, the inkjet head includes a vibrating mechanism that is placed in the ink flow channel and that vibrates a supplied ink.

According to the above structure, a driving force from the piezoelectric element is transmitted to the pressure chamber via the diaphragm, and thus, it becomes possible to discharge a solution including cells.

Furthermore, since the mechanism that vibrates a solution including cells is provided, the solution including cells is vibrated to thereby agitate precipitated cells, and this makes it possible to disperse homogenously the cells in the solution.

DESCRIPTION OF EMBODIMENTS

Prior to description of embodiments of the disclosure, problems in a conventional inkjet head will briefly be described. When a solution including cells or the like is discharged by use of multiple nozzles in a conventional inkjet head, the solution including particles or the like such as cells will cause the sedimentation of the particles if the solution is left to stand. Furthermore, it is difficult to supply cells evenly to the multiple nozzles inside the inkjet head.

Therefore, in order to suppress the sedimentation of particles in the solution, a method in which the concentration of the solution is modified to suppress the precipitation of the particles, and the solution including particles is circulated has also been proposed.

However, materials having low hardness (e.g. cells) are easily stuck in pumps during the circulation. If the cells are stuck in pumps, cells will be damaged.

Hereinafter, embodiments of the disclosure will be described with reference to the drawings.

First Embodiment

Figure 1A:
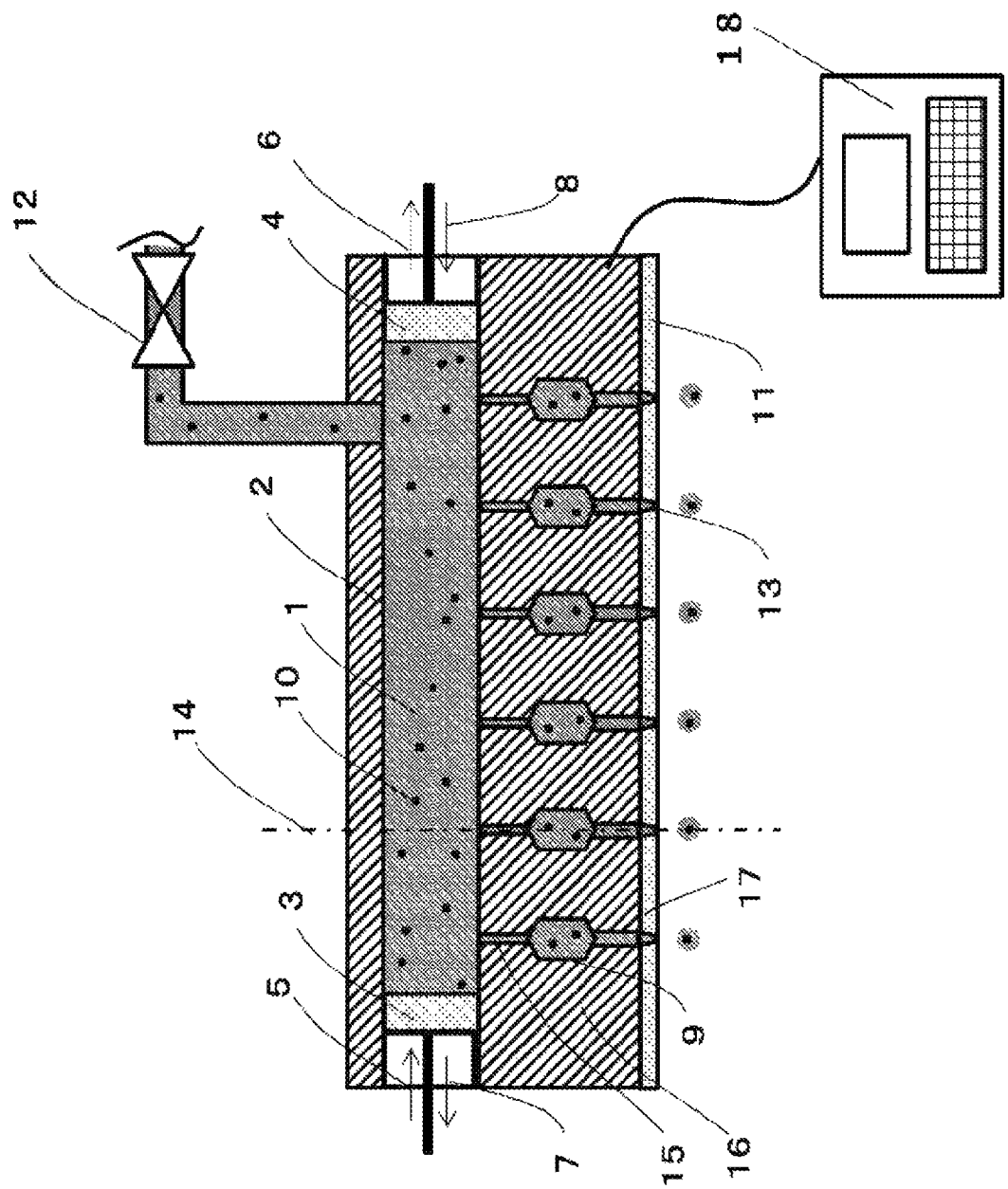
FIG. 1A is a cross-section diagram of an inkjet head according to a first embodiment.
Figure 1B:
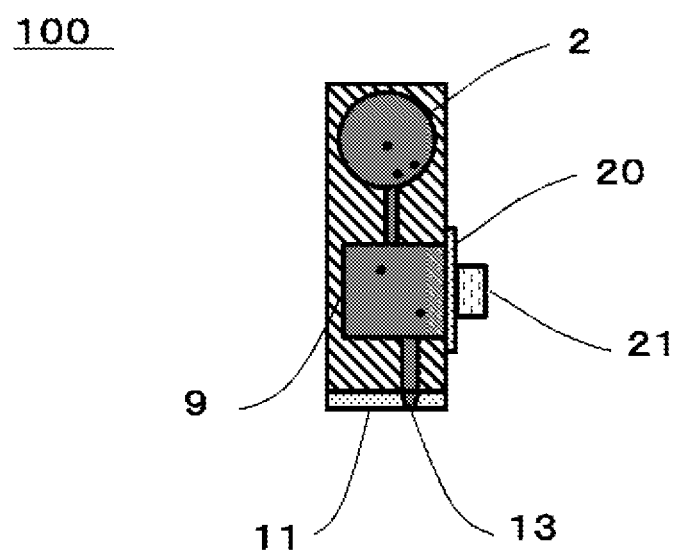
FIG. 1B is a cross-section diagram of the inkjet head according to the first embodiment.

FIG. 1A shows a vibrating-type inkjet head 100 according to an embodiment. FIG. 1B is a cross-section of the inkjet head 100 along the line 14.

<Structure>

The inkjet head 100 according to this embodiment includes: a pipe-shaped vessel 2; multiple flow channels 15 that are branched from the vessel 2; multiple pressure chambers 9 that are connected to the vessel 2 via the respective flow channels 15; flow channels 17 that are connected to outlet sides of the respective pressure chambers 9; nozzles 13 that correspond to respective outlets of the flow channels 17; and a control unit 18.

The pipe-shaped vessel 2 is a flow channel (ink flow channel) through which an ink flows, retains the ink, and supplies the ink to each of the multiple flow channels 15. The pressure chambers 9 are rooms in each of which a pressure for discharging the ink toward the outside is applied to the ink.

As shown in FIG. 1B, a piezoelectric element 21 is attached to each of the pressure chambers 9 via a diaphragm 20. Furthermore, cylinders 3 and 4 are placed at both sides of the pipe-shaped vessel 2. The cylinders 3 and 4 form a vibrating mechanism that changes positions of both edges of the vessel 2. Additionally, it is possible to supply a solution 1 to the pipe-shaped vessel 2 via a valve 12.

<Conditions for Process>

A rate of movement (vibrating) of cylinders 3 and 4 is preferably about 0.01-100 mm/s. The rate is particularly preferably about 0.11-10 mm/s. If the rate is smaller than 0.1 mm/s, cells 10 may not sufficiently be moved. If the rate is larger than 100 mm/s, cells 10 may be damaged.

The cylinder 3 is preferably moved immediately interior to the position of the leftmost flow channel 15 in FIG. 1A. Additionally, the cylinder 4 is also preferably moved immediately interior to the position of the rightmost flow channel 15 in FIG. 1A. If the cylinders 3 and 4 exceed the positions of these flow channels 15, the air, etc. may penetrate into flow channels 15, and that may cause adverse effects on the cells 10.

Moreover, in order to observe a state of vibrating of cells 10, the pipe-shaped vessel 2 is preferably formed of a transparent material, and the agitating state is preferably monitored by a camera. Actually, based on movement of the cylinders 3 and 4, it can be confirmed whether the cells 10 are moved. The moving conditions can be set according to a type and a concentration of the cells 10.

Furthermore, agitation of cells 10 can be carried out when the solution 1 is discharged. Only in cases where the cells 10 are hardly included in the discharged solution 1, the cylinders 3 and 4 may be moved. The vessel 2 and flow channels 17 are located apart from each other, and movement of the cylinders 3 and 4 does not cause any effects on the discharge from the inkjet head 100.

The reason why the cells 10 are vibrated is to prevent the cells 10 from precipitating and adhering onto the pipe-shaped vessel 2 over time. Therefore, when the cells 10 are not adhered to the pipe-shaped vessel 2, it is not necessarily required that the movement of the cylinders 3 and 4 are actively conducted.

For cells 10 for an experimental purpose, mouse cells can be used. The size of the cells is about 10-20 µm. The concentration of the cells 10 is preferably about $10^4$-$10^8$ cells/mL. For the solution 1 into which cells 10 have been mixed, a culture medium is used, and the viscosity thereof is 1-5 mPa·s.

If the concentration of the cells 10 is lower than $10^4$ cells/mL, a probability of emission of the cells 10 by the discharge from the inkjet head 100 becomes low. If the concentration is higher than $10^8$ cells/mL, cells 10 collide against one another, the possibility of disruption of the cells 10 will be higher, and this likely causes clogging of nozzles 13 in the inkjet head 100.

The higher the concentration of the cells 10, the more actively the vibrating movement using the cylinders is preferably conducted. Preferably, the vibrating movement is carried out when the concentration of cells is $10^6$ cells/mL or more.

In addition, the control unit 18 controls the inkjet head 100, i.e., controls movement of the cylinder 3, operation of the piezoelectric element 21, etc. The control unit 18 is a control device that includes a semiconductor element.

<Process>

The solution including cells 10 is injected into the pipe-shaped vessel 2 via the valve 12. Following the valve 12, a filter may be placed. When the size of cells is 20 µm or less, for example, a filter of 20 µm or less may be used. By using such a filter, it becomes possible to inject cells having a size of 20 µm or less.

When the cylinders 3 and 4 are brought into contact with the solution 1, there is a risk of contamination of air bubbles, etc. Therefore, when such air bubbles are present, the air bubbles, or a solution 1 including air bubbles is discharged from the valve 12, or nozzles 13 in the inkjet head. After the air bubbles or the solution 1 including air bubbles is discharged, the cylinders 3 and 4 are brought into contact with the injected solution.

When the cylinder 3 moves toward the direction shown by the arrow 5, the cylinder 4 also moves toward the direction shown by the arrow 6 in tandem with the cylinder 3. Furthermore, when the cylinder 3 moves toward the direction shown by the arrow 7, the cylinder 4 moves toward the direction shown by the arrow 8. Thus, by causing the cylinder 3 and 4 to move toward the same direction in tandem with each other, the solution 1 including cells 10 is prevented from receiving excessive pressure. If the pressure becomes excessively low, there is high possibility that air bubbles likely contaminate the solution 1. If the pressure becomes excessively high, there is high possibility that the solution 1 seeps through the nozzles 13 in the inkjet head, and the discharge from the nozzles 13 in the inkjet head becomes unstable. That is, by causing the cylinders 3 and 4 to move toward the same direction, it becomes possible to agitate the cells 10. By agitating the cells 10, it becomes possible to suppress sedimentation of the cells 10.

Moreover, in cases where there are multiple pressure chambers 9 in the inkjet head, it becomes possible to supply solutions 1 including even densities of cells to the pressure chambers 9.

Furthermore, in this embodiment, since the vibrating movement in which the cylinders 3 and 4 hardly causing changes in the pressure of the solution 1 are moved is utilized, no damages are caused to the cells 10. In general, if a tube pump, which extrudes a tube, a diaphragm pump, etc. are used for carrying out the circulation, there is a risk of disruption of cells during rotation of the pump.

The solution 1 including cells 10 homogenized by the vibrating movement of the cylinders 3 and 4, etc. enters pressure chambers 9 through the flow channels 15, and is discharged from the nozzles 13.

In this embodiment, a nozzle plate 11 in which the nozzles 13 have been formed by high-precision processing is attached to the body 16 of the inkjet. In cases where a solution 1 including cells 10 is used, disposable materials are preferable, and therefore, the body 16 of the inkjet is preferably made of a resin.

For the resin, acrylic, polyethylene, COP materials (cycloolefin polymer), etc. are preferable. Furthermore, the nozzle plate 11 is preferably made of the same resin material as the body 16 of the inkjet. This is because, by using the same resin material for these parts, the body 16 of the inkjet, and the nozzle plate 11 can be joined by way of a process of fusion or the like.

The flow channels 15 and 17 may be formed by hole-drilling using a drill, etc. Additionally, a nozzle(s) may be formed in the nozzle plate 11 by carrying out high-precise processing against a metal such as a stainless steel (e.g. SUS304). This is because high-precise nozzle processing can be carried out by using laser. In a case where the nozzle plate 11 is formed by processing of a metal, the nozzle plate 11 is preferably joined to the body 16 of the inkjet by a process of adhesion, etc. For example, when a diameter of the cells is 20 µm, the diameter of the nozzles 13 is preferably about 50-70 µm. This is because, if the diameter of the nozzles 13 is smaller than 50 µm, the cells are likely to stick in the nozzles, and, if the diameter of the nozzles 13 is larger than 70 µm, a degree of the discharging precision becomes inferior when droplets including cells are spotted on a certain object.

As shown in FIG. 1B, the piezoelectric element 21 is in contact with the rear of the pressure chamber 9 via the diaphragm 20. For the diaphragm 20, a resin may be used, or a metal such as nickel, nickel cobalt, and palladium may be used. By activating the piezoelectric element 21, the diaphragm 20 bends, and the volume of the pressure chamber 9 varies, and the solution 1 is discharged from the nozzle 13. The piezoelectric element 21 may be formed by adhesion of a thin film of PZT through sputtering or the like, or may be formed by lamination (e.g., a bulk piezoelectric element).

Second Embodiment

Figure 2:
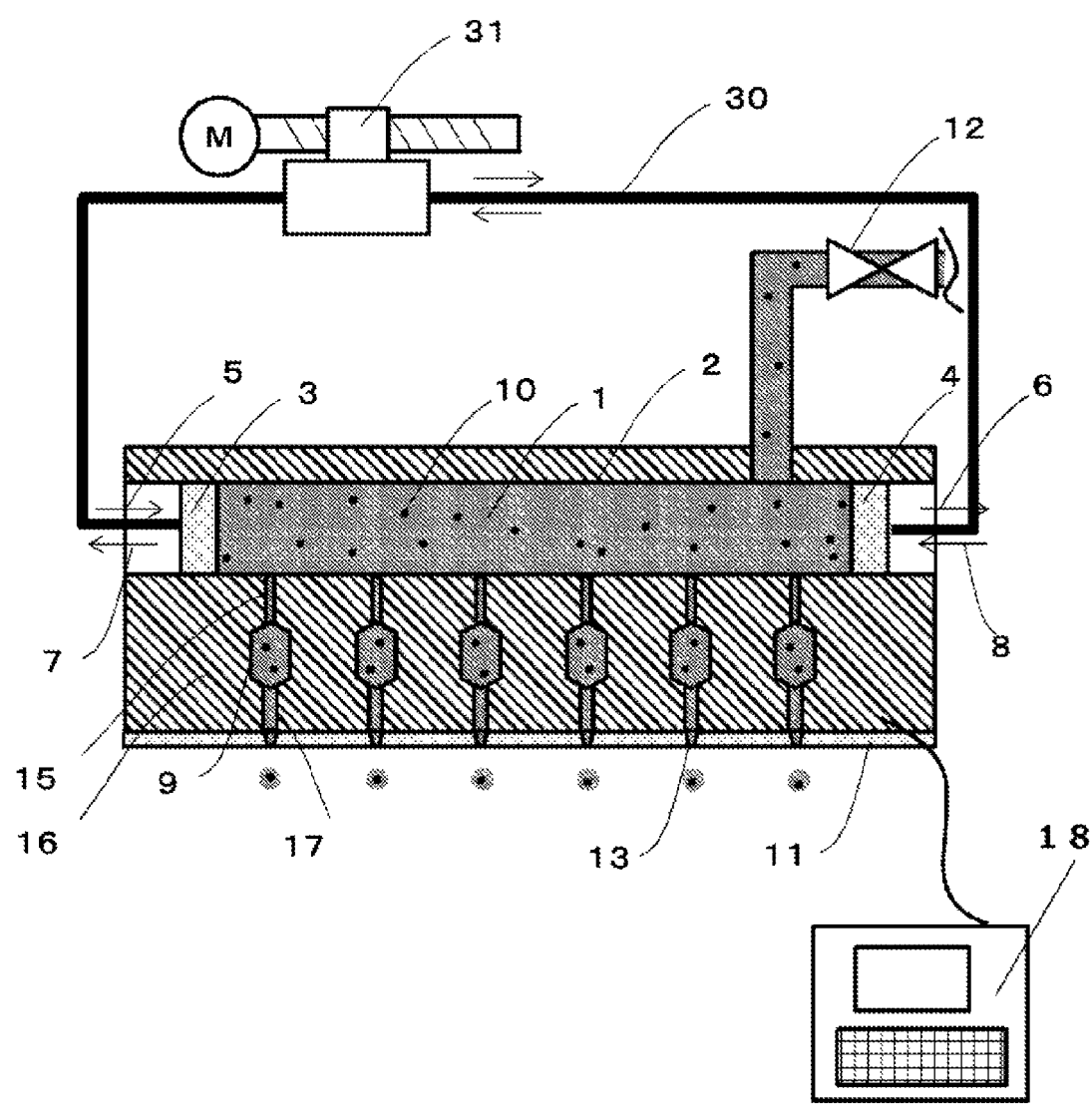
FIG. 2 is a cross-section diagram of an inkjet head according to a second embodiment.

FIG. 2 shows a vibrating-type inkjet head 200 according to the second embodiment of the disclosure. A difference between the second embodiment and the first embodiment is that the cylinders 3 and 4 are joined through a joint 30 in order to force these members to move to the same direction. Other matters not described in the second embodiment are the same as the first embodiment.

The joint 30 is attached to a ball screw 31 that is coupled to a motor. By causing the ball screw 31 to move forward and backward (right-to-left direction in FIG. 2), the joint 30 can be moved. By moving the joint 30, the cylinders 3 and 4 can be moved, and the solution 1 including cells 10 can be agitated. Thus, it becomes possible to suppress sedimentation of cells 10.

In this method, the cylinders 3 and 4 are physically connected with each other, and thus, are moved simultaneously. Matters not mentioned are the same as the first embodiment.

Third Embodiment

Figure 3:
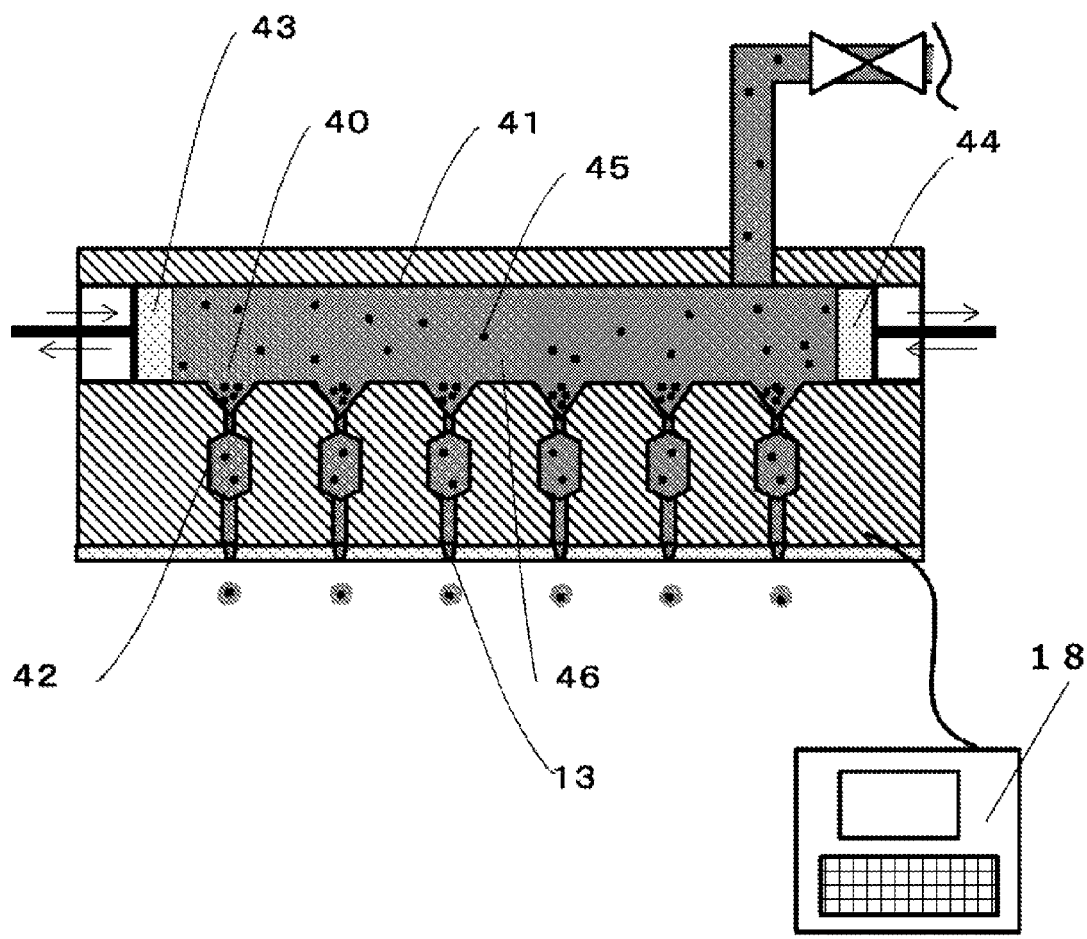
FIG. 3 is a cross-section diagram of an inkjet head according to a third embodiment.

FIG. 3 shows a cross-section diagram of an inkjet head 300 according to the third embodiment. The third embodiment differs from the first and second embodiments in that, in the third embodiment, hollows 40 are each provided above flow channels that lead to respective pressure chambers 42, inside a pipe-shaped vessel 41. That is, the hollows 40 are each provided around inlets of the flow channels that lead from the vessel 41, which serves as a common ink chamber, to the multiple pressure chambers 42. A shape of each of the hollows 40 may be any of a cone, pyramid, cylinder, and prismatic column. Preferably, the cross-section area of each of the hollows 40 on the horizontal plane becomes smaller toward the downward direction. Each of the hollows 40 is preferably conical.

By vibrating a solution 46 including cells 45 based on cylinders 43 and 44, the probability of entry of the cells 45 to the hollows 40 becomes high. Therefore, certain equal amounts of the cells 45 are accumulated in the respective inlets of the pressure chambers 42. The cells 45 that have not entered the hollows 40 float in the solution 46. The cells that have entered the hollows 40 are led to the pressure chambers 42, and are discharged from the nozzles 13. By provision of hollows 40, in such a structure the cells 45 easily enter the hollows 40, and certain amounts of the cells 45 are retained inside the respective hollows 40. This makes it possible to supply the cells 45 homogenously to the pressure chambers 42. Matters not described in the third embodiment are the same as the first or second embodiment.

Furthermore, by providing, in the vessel 41, the cylinders 43 and 44 that serve as a mechanism for vibrating the solution 41 including cells 45, the solution including cells 45 can be vibrated, and cells 45 that have been precipitated on parts other than the hollows 40 can be agitated, to thereby homogenously disperse the cells 45 in the solution.

Fourth Embodiment

Figure 4A:
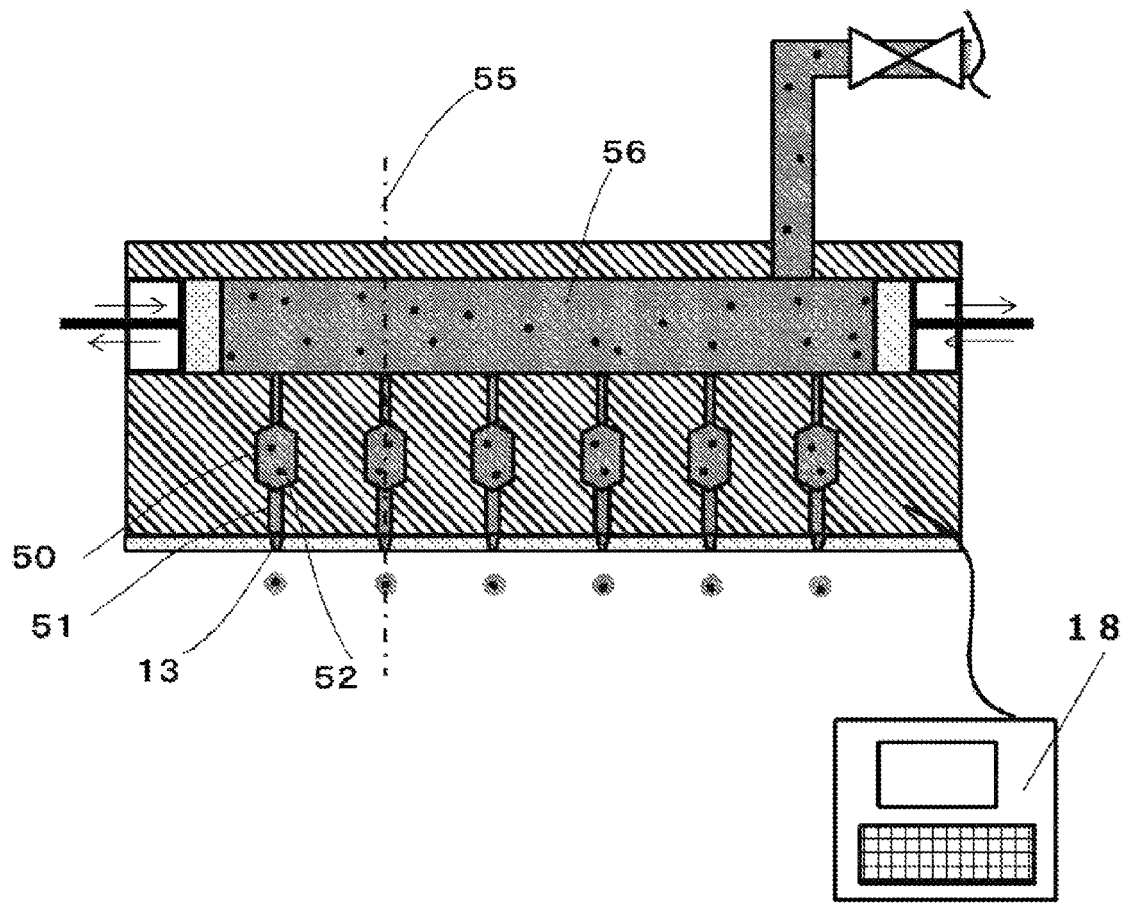
FIG. 4A is a cross-section diagram of an inkjet head according to a fourth embodiment.
Figure 4B:
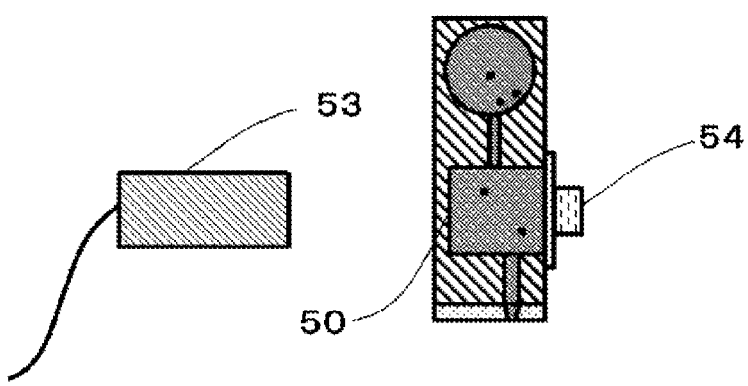
FIG. 4B is a cross-section diagram of the inkjet head according to the fourth embodiment.

FIGS. 4A and 4B are cross-section diagrams of an inkjet head 400 according to the fourth embodiment. FIG. 4B is a cross-section diagram thereof along the line 55 in FIG. 4A.

The fourth embodiment differs from the first to third embodiments in that walls of pressure chambers 50 are formed of a transparent material to observe states of the pressure chambers 50 by a camera(s) 53. Based on the observation, piezoelectric elements 54 are controlled. The results of the observation are input to a control unit 18, and each of the piezoelectric elements 54 is controlled by the control unit 18.

Other matters not described in the fourth embodiment are the same as the first embodiment. In cases where cells 52 are present in inlets around flow channels 51, i.e., in boundaries between the pressure chambers 50 and the flow channels 51, each piezoelectric element 54 is activated to discharge the solution 56 including cells 52. Additionally, hollows (not shown in the figures) may be provided between the respective pressure chambers 50 and the flow channels 51 so as to cause the cells to easily accumulate therein.

In FIG. 4B, when any cells 52 are not present, the piezoelectric element 54 may be caused to vibrate to an extent that the solution 56 will not be discharged, to thus agitate the solution 56 inside pressure chamber 50. Alternatively, when any cells 52 are not present, the piezoelectric element 54 may be put in a standby mode, i.e., may not be vibrated. Furthermore, even when any cells 52 are not present, test coating may be conducted by using the piezoelectric element 54. The term "test coating" refers to discharging a solution 56 not including any cells against a spot other than target spots onto which the solution should be coated.

In this manner, by discharging predetermined cells 52 onto a desired location, it becomes possible to form a three-dimensional shape of the cells 52. Although the inkjet head 400 that discharge the cells 52 is used in this embodiment, the solution 56 including cells 52 may be discharged, and then, extracellular matrices may be discharged by the inkjet head 400. By discharging also extracellular matrices after discharge of the cells, it becomes possible to promote binding of cells 52.

The term "extracellular matrix (matrices)" have a role as a scaffold for cell-cell adhesion. The extracellular matrix (matrices) rigidly fixes cells.

As embodiments of extracellular matrices, a basement membrane, and fibronectin can be mentioned.

Moreover, in order to form a three-dimensional structure of cells, it is required that multiple types of cells 52 are discharged. When multiple types of cells 52 need to be discharged, an inkjet heads 400 may be provided with respect to each type of cells 52, and the different types of the cells 52 may be loaded into the respective inkjet heads 400. Then, any of these cells 52 may be discharged so as to form a three-dimensional shape.

Furthermore, although, in this example, the same type of cells 52 are loaded into one single inkjet head 400, and the solution 56 including the cells 52 is discharged therefrom, multiple types of cells 52 may be loaded into one single inkjet head 400, and thus, a solution 56 including these cells 52 may be discharged therefrom.

Fifth Embodiment

Figure 5:
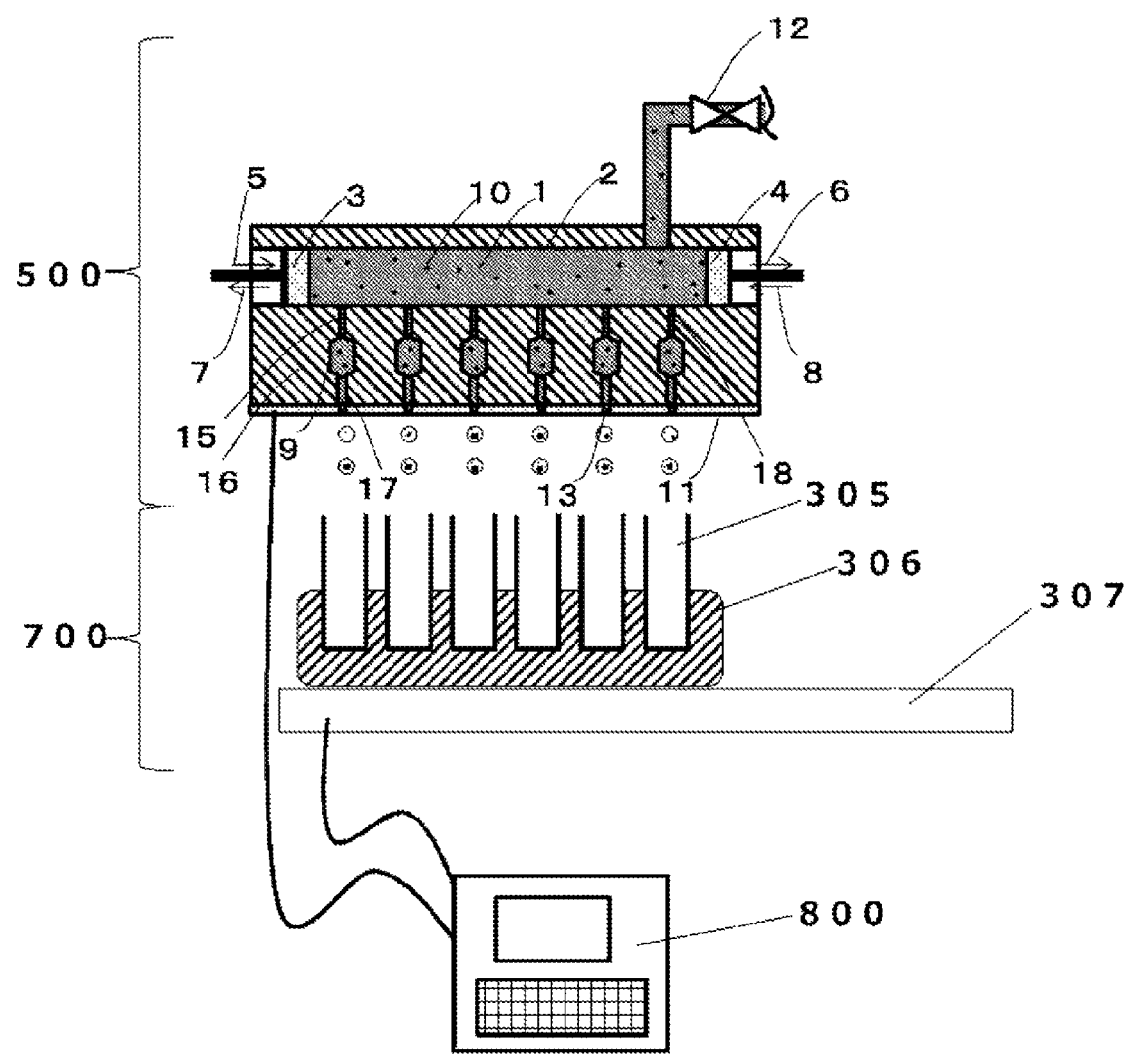
FIG. 5 is a cross-section diagram of an inkjet device according to a fifth embodiment.

FIG. 5 refers to an inkjet device 600 according to the fifth embodiment of the disclosure. The inkjet device 600 includes an inkjet head 500 and a subject-moving mechanism 700.

For the inkjet head 500, the above-described inkjet head 100 according to the embodiment is used. Any one or a plurality of the inkjet heads 100, 200, 300 and 400 can be used.

The subject-moving mechanism 700 includes test tubes 305 (which corresponds subjects), a test tube holder 306, and a test tube holder-moving mechanism 307.

In this device, an ink is supplied simultaneously to the multiple test tubes 305. The test tubes 305 move together with the test tube holder 306.

Instead of the subject-moving mechanism 700, the inkjet head 500 may be moved. It would be sufficient if any mechanism that makes it possible to cause relative movement between the subject-moving mechanism 700 and the inkjet head 500 may be used. However, since the mechanism of the inkjet head 500 is complex, the inkjet head 500 is preferably fixed.

The inkjet device 600 is configured by the inkjet head 500, test tubes 305, a test tube holder 306 that serves as a holding unit for holding a subject, a test tube holder-moving mechanism 307 that serves as a moving mechanism for causing relative movement between the inkjet head 500 and the holding unit, and a control unit 800 that controls these members.

An device for coating various solutions can be realized by using the above inkjet heads. In addition, the above-described embodiments can be combined.

By using an inkjet head of the disclosure, it becomes possible to suppress precipitation of cells in a solution including the cells, and, even if the inkjet head has multiple nozzles, it becomes possible to evenly supply the cells to the nozzles. An inkjet head according to the disclosure can also be utilized for coating a solution including particles other than cells, or for coating multiple solutions.

What is claimed is:

1. An inkjet head, comprising:
    a pressure chamber that is communicated with an ink flow channel;
    a diaphragm that is linked to the pressure chamber;
    a piezoelectric element that is linked to the diaphragm;
    a nozzle that is communicated with the pressure chamber; and
    a vibrating mechanism that is placed in the ink flow channel and that vibrates a supplied ink,
    wherein the vibrating mechanism does not change an ink pressure of the ink flow channel while vibrating the supplied ink.

2. The inkjet head according to claim 1, wherein the vibrating mechanism is a mechanism that individually changes positions of both edges of the ink flow channel.

3. The inkjet head according to claim 1, wherein the vibrating mechanism is a mechanism that simultaneously changes the positions of the both edges of the ink flow channel.

4. The inkjet head according to claim 1, wherein a hollow is provided between the ink flow channel and the pressure chamber and a cross-sectional area of the hollow on a horizontal plane becomes smaller toward a downward direction.

5. The inkjet head according to claim 1, further comprising:
    an observation unit that observes the ink in the pressure chamber by a camera; and
    a control unit that controls the piezoelectric element based on results obtained by the observation unit.

6. The inkjet head according to claim 1, further comprising multiple flow channels that are communicated with the ink flow channel, wherein the pressure chamber, the diaphragm, the piezoelectric element, and the nozzle are provided in each of the multiple flow channels.

7. The inkjet head according to claim 1, further comprising cells that are included in the ink.

8. An inkjet device, comprising:
    the inkjet head according to claim 1;
    a holding unit that holds a subject;
    a moving mechanism that causes relative movement between the inkjet head and the holding unit; and
    a control unit that controls the inkjet head, the holding unit, and the moving mechanism.

9. The inkjet head according to claim 1, wherein the vibrating mechanism includes a pair of cylinders.

10. The inkjet head according to claim 1, wherein a pair of the vibrating mechanisms are provided at both ends of the ink flow channel and move in the same direction with respect to the flow of the ink.

11. The inkjet head according to claim 1, wherein the ink flow channel is one straight pipe shape and the vibrating mechanism is provided at both ends of the ink flow channel.

12. The inkjet head according to claim 1, wherein the ink flow channel is formed of a transparent material.

13. The inkjet head according to claim 1, wherein a wall of the pressure chamber is formed of a transparent material.

* * * * *